United States Patent
Masaki et al.

(10) Patent No.: US 9,326,674 B2
(45) Date of Patent: May 3, 2016

(54) OPTICAL TOMOGRAPHIC IMAGING APPARATUS AND METHOD FOR CONTROLLING THE SAME

(71) Applicant: CANON KABUSHIKI KAISHA, Tokyo (JP)

(72) Inventors: Toshifumi Masaki, Tokyo (JP); Hiroshi Aoki, Saitama (JP); Yukio Sakagawa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 66 days.

(21) Appl. No.: 14/161,539

(22) Filed: Jan. 22, 2014

(65) Prior Publication Data

US 2014/0211156 A1 Jul. 31, 2014

(30) Foreign Application Priority Data

Jan. 31, 2013 (JP) ................................. 2013-017659

(51) Int. Cl.
*A61B 3/14* (2006.01)
*A61B 3/10* (2006.01)
*A61B 3/00* (2006.01)

(52) U.S. Cl.
CPC .............. *A61B 3/0033* (2013.01); *A61B 3/102* (2013.01)

(58) Field of Classification Search
USPC ................................................ 351/200–246
See application file for complete search history.

(56) References Cited

U.S. PATENT DOCUMENTS

| 8,960,904 B2 | 2/2015 | Aoki et al. |
| 8,960,905 B2 | 2/2015 | Aoki et al. |
| 2008/0151256 A1* | 6/2008 | Kikawa ..................... A61B 3/10 356/496 |
| 2013/0107272 A1* | 5/2013 | Hirose .......................... 356/477 |
| 2013/0107277 A1* | 5/2013 | Hirose ................... A61B 3/102 356/512 |
| 2013/0194545 A1* | 8/2013 | Ono .............................. 351/206 |
| 2014/0211158 A1* | 7/2014 | Oyaizu .................. A61B 3/102 351/206 |
| 2015/0055091 A1* | 2/2015 | Ikegami ....................... 351/206 |

FOREIGN PATENT DOCUMENTS

| CN | 1413552 A | 4/2003 |
| CN | 101411608 A | 4/2009 |
| CN | 102727174 A | 10/2012 |
| CN | 103222850 A | 7/2013 |
| CN | 103251380 A | 8/2013 |
| JP | 2009-160190 A | 7/2009 |
| JP | 2011147612 A | 8/2011 |

\* cited by examiner

*Primary Examiner* — Mohammed Hasan
(74) *Attorney, Agent, or Firm* — Canon USA Inc. IP Division

(57) ABSTRACT

An optical tomographic imaging apparatus includes a measurement light optical path length changing unit configured to change an optical path length of measurement light. In a case where any one of a plurality of imaging regions of an object (for example, a region of an anterior eye of a subject's eye and a region of a fundus of the subject's eye) is selected, the optical tomographic imaging apparatus can control the measurement light optical path length changing unit according to a size of an imaging range of a tomographic image corresponding to the selected imaging region.

18 Claims, 15 Drawing Sheets

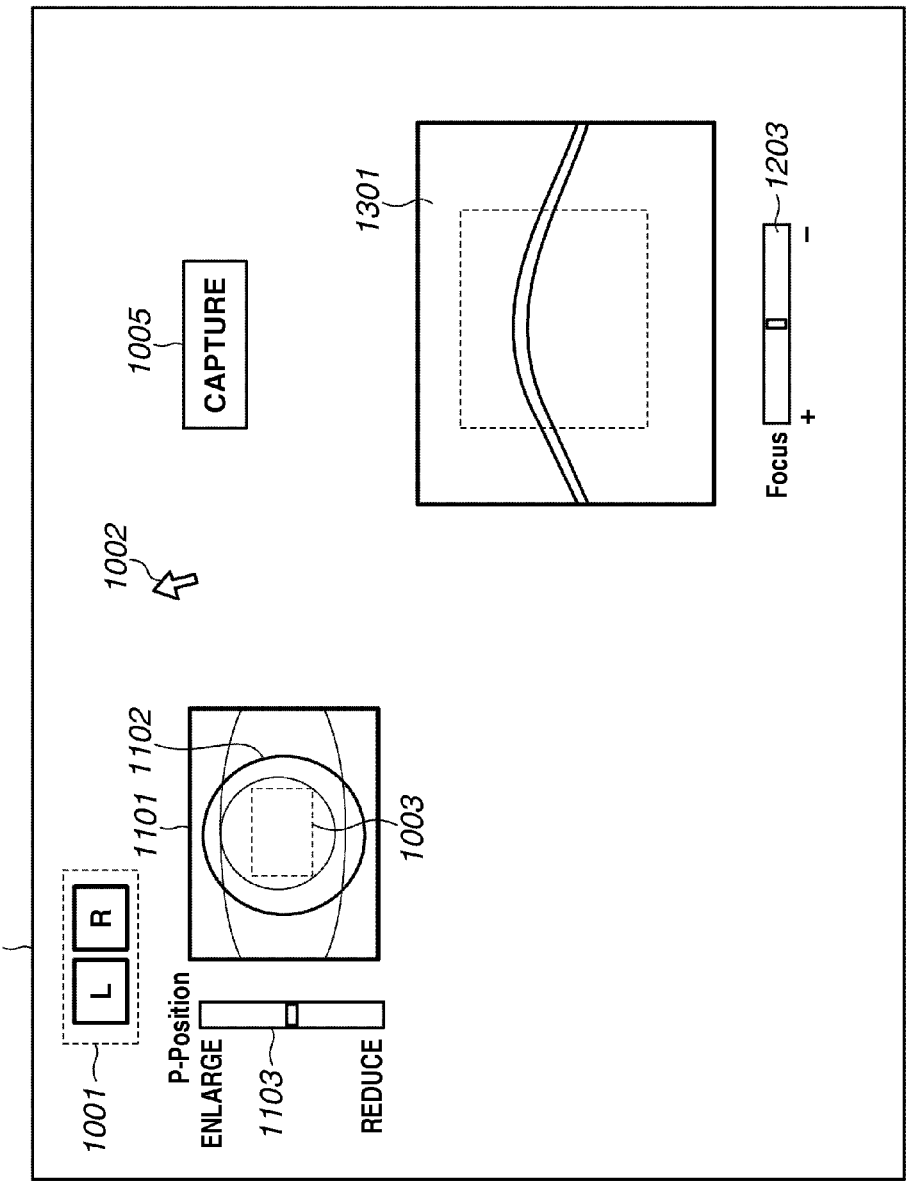

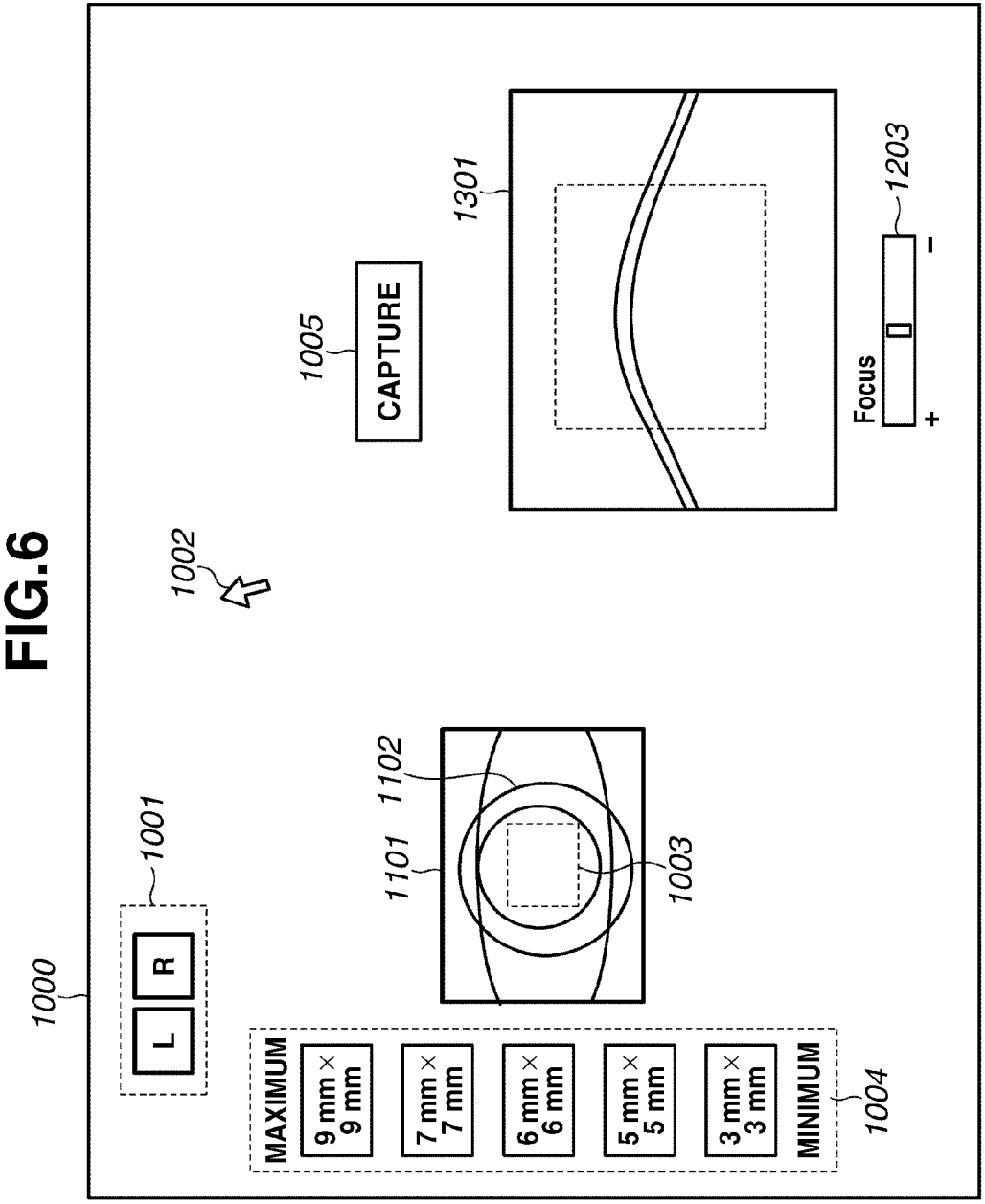

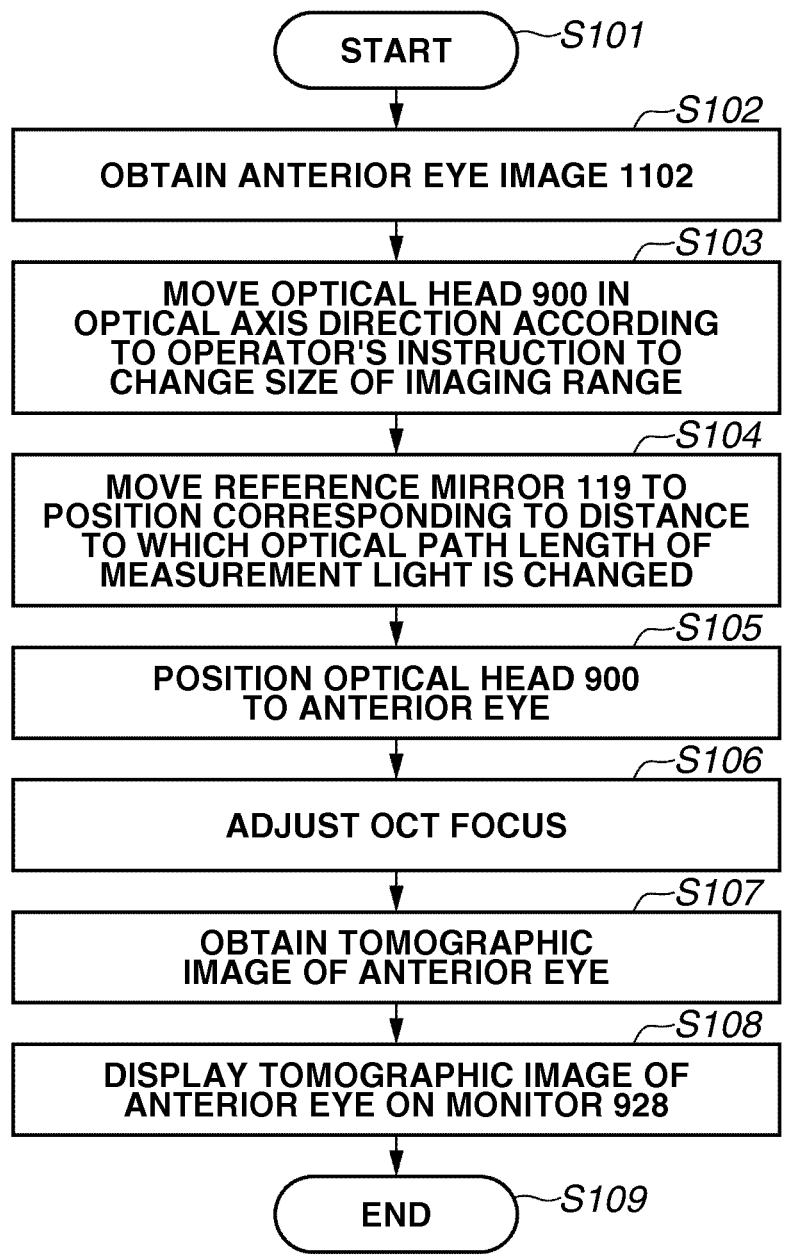

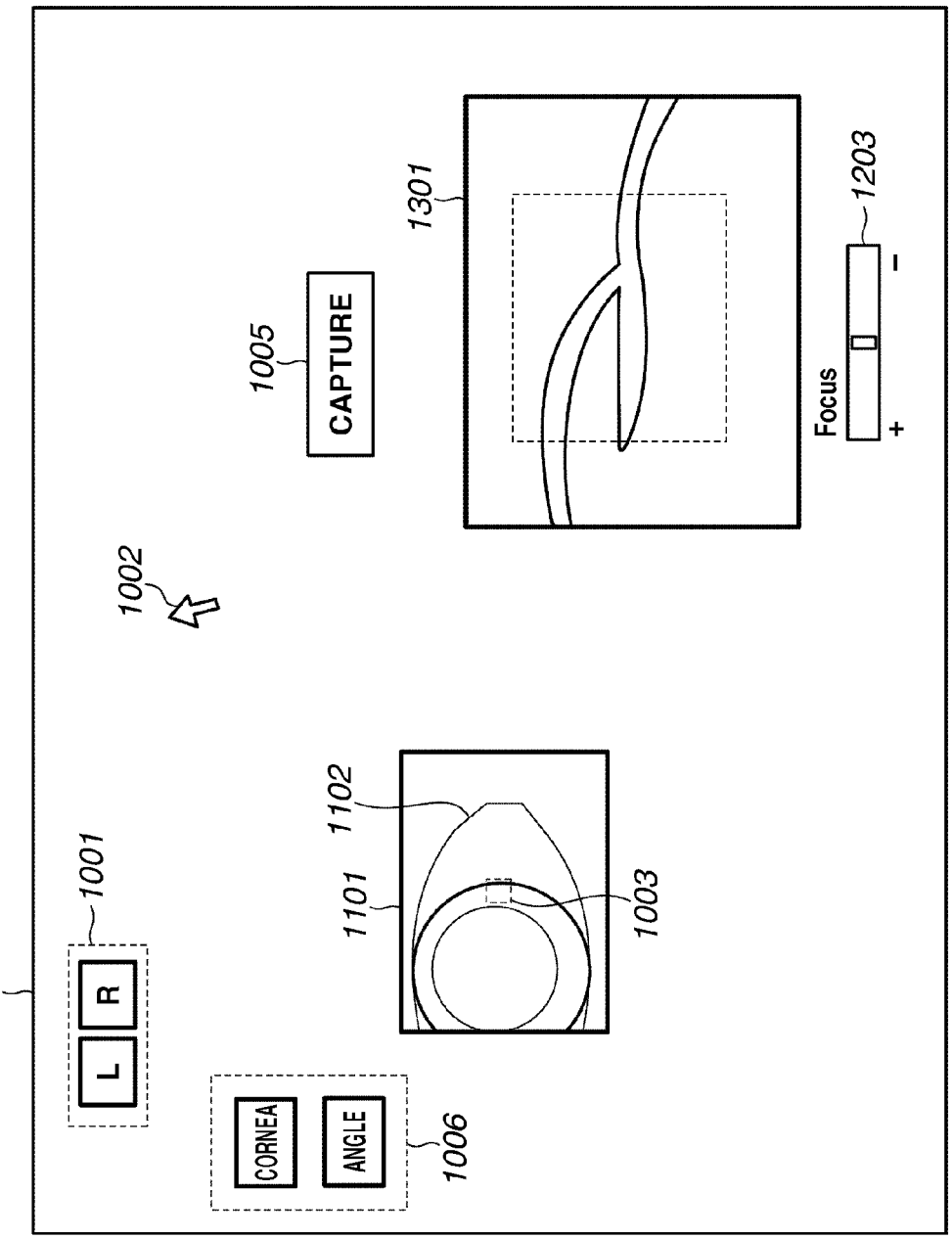

OPTICAL TOMOGRAPHIC IMAGING APPARATUS AND METHOD FOR CONTROLLING THE SAME

BACKGROUND OF THE INVENTION

1. Field of the Invention

The present invention relates to an optical tomographic imaging apparatus and a method for controlling the same. For example, the present invention relates to an optical tomographic imaging apparatus for use in ophthalmic practice and a method for controlling the same.

2. Description of the Related Art

Optical image measurement techniques for forming an image of the surface and/or inside of an object to be measured by using light are attracting attention in recent years. Unlike conventional X-ray computed tomography (CT), the optical image measurement techniques are not invasive to the human body. Applications of the optical image measurement techniques are expected to be developed especially in the medical field. Significant progress has been made in the ophthalmological field in particular.

Among typical techniques for optical image measurement is a method called optical coherence tomography (OCT). This method uses an interferometer, which enables high-resolution high-sensitivity measurement. Using wideband weak light as illumination light provides an advantage of high safety to a subject.

An optical tomographic imaging apparatus based on OCT (hereinafter, referred to as an OCT apparatus) using optical interference can obtain a tomographic image of a sample with high resolution. In particular, the OCT apparatus relates to an anterior eye optical tomographic imaging apparatus for forming an image of an anterior eye of a subject's eye.

The OCT apparatus can irradiate a sample with low coherent light serving as measurement light, and measure backscattered light from the sample with high sensitivity by using an interference system or an interference optical system. The OCT apparatus can scan the sample with the measurement light to obtain a high-resolution tomographic image. A tomographic image of a cornea region of the anterior eye of a subject's eye can thus be obtained and used for ophthalmic diagnosis.

Japanese Patent Application Laid-Open No. 2011-147612 discusses an optical tomographic imaging apparatus that can capture both a tomographic image of an anterior eye and a tomographic image of a fundus. According to whether an imaging mode is an anterior eye imaging mode or a fundus imaging mode, the optical tomographic imaging apparatus moves a reference mirror included in its interference optical system to a position corresponding to the imaging mode.

SUMMARY OF THE INVENTION

According to an aspect of the present invention, an optical tomographic imaging apparatus configured to obtain a tomographic image of an object based on light into which return light from the object irradiated with measurement light and reference light corresponding to the measurement light are combined includes a measurement light optical path length changing unit configured to change an optical path length of the measurement light, a selection unit configured to select any one of a plurality of imaging regions of the object, and a control unit configured to control the measurement light optical path length changing unit according to a size of an imaging range of the tomographic image corresponding to the selected imaging region.

Further features of the present invention will become apparent from the following description of exemplary embodiments with reference to the attached drawings.

BRIEF DESCRIPTION OF THE DRAWINGS

FIG. 5 is a diagram illustrating an example of a measurement operation screen according to the first exemplary embodiment.

FIG. 6 is a diagram illustrating another example of the measurement operation screen according to the first exemplary embodiment.

FIG. 7 is a flowchart illustrating a measurement flow according to the first exemplary embodiment.

FIG. 9 is a diagram illustrating an example of a measurement operation screen according to a second exemplary embodiment.

DESCRIPTION OF THE EMBODIMENTS

Figure 1:
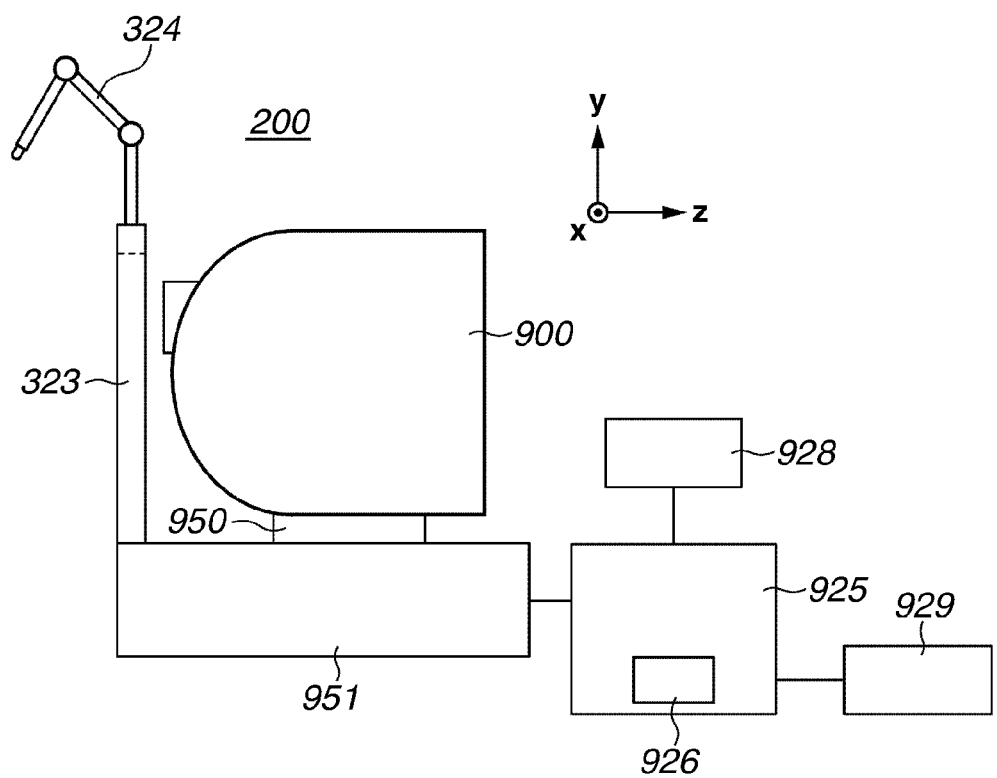
FIG. 1 is a diagram illustrating an entire optical tomographic imaging apparatus according to a first exemplary embodiment.

Take the case of changing the size of the imaging range of a tomographic image of an object such as a subject's eye. A possible method may include changing the optical path length of measurement light by moving the apparatus main body with respect to the object in an optical axis direction. With such a method, an operator cannot readily know how much the optical path length of the measurement light is to be changed to obtain a tomographic image of the size intended by the operator.

An exemplary embodiment of the present invention is directed to easily obtaining a tomographic image of the intended size by the operator specifying the size of the imaging range of the tomographic image of the object.

An optical tomographic imaging apparatus according to the present exemplary embodiment includes a measurement light optical path length changing unit configured to change an optical path length of measurement light. In a case where any one of a plurality of imaging regions of an object (for example, a region of an anterior eye of a subject's eye and a region of a fundus of the subject's eye) is selected, the optical tomographic imaging apparatus can control the measurement light optical path length changing unit according to a size of an imaging area of a tomographic image corresponding to the selected imaging region. As a result, the operator can easily obtain a tomographic image of the intended size by designating the size of the imaging range of the tomographic image of the object.

The plurality of imaging regions can include at least either one of a cornea and an iridocorneal angle of an anterior eye of a subject's eye. The optical tomographic imaging apparatus can control the measurement light optical path length changing unit to increase the optical path length of the measurement light in a case where the cornea is selected as the imaging region. This can locate an optical head farther from the subject's eye, so that the cornea can be imaged over a wide range. The optical tomographic imaging apparatus can control the measurement light optical path length changing unit to decrease the optical path length of the measurement light in a case where the iridocorneal angle is selected as the imaging region. This can locate the optical head closer to the subject's eye, so that the iridocorneal angle can be magnified and imaged in detail.

The plurality of imaging regions can include at least either one of a macula and an optic disc of a subject's eye. The optical tomographic imaging apparatus can control the measurement light optical path length changing unit to increase the optical path length of the measurement light in a case where the macula is selected as the imaging region. This can locate the optical head farther from the subject's eye, so that a fundus including the macula can be imaged over a wide range. The optical tomographic imaging apparatus can control the measurement light optical path length changing unit to decrease the optical path length of the measurement light in a case where the optic disc is selected as the imaging region. This can locate the optical head closer to the subject's eye, so that the optic disc can be magnified and imaged in detail.

An optical tomographic imaging apparatus (OCT apparatus) according to a first exemplary embodiment will be described below with reference to the drawings.

[General Configuration of Apparatus]

A general configuration of the optical tomographic imaging apparatus according to the present exemplary embodiment will be described with reference to FIG. 1. FIG. 1 is a side view of the optical tomographic imaging apparatus. The optical tomographic imaging apparatus 200 includes an optical head 900 which includes a measurement optical system for capturing a two-dimensional image and a tomographic image of an anterior eye. A stage unit 950 is a moving unit that can move the optical head 900 in x, y, and z directions in the diagram by using not-illustrated motors. A base unit 951 includes a spectroscope to be described below. The optical head 900, an example of an optical unit including an optical path of measurement light, is a housing of the measurement optical system. The stage unit 950 is an example of an optical unit moving mechanism that moves with respect to an object.

A personal computer 925 constructs a tomographic image. The personal computer 925 also serves as a control unit of the stage unit 950 and controls the stage unit 950. A hard disk 926 stores a program for tomographic imaging. The hard disk 926 also serves as a subject information storage unit. A monitor 928 serves as a display unit. An input unit 929 is used to give instructions to the personal computer 925. Specifically, the input unit 929 includes a keyboard and a mouse. A chin rest 323 fixes the chin and forehead of a subject to prompt the subject to fix the eyes (subject's eyes). An external fixation lamp 324 is used to fix the subject's eyes. The external fixation lamp 324 and an internal fixation lamp to be described below can be switched and used.

[Configuration of Measurement Optical System and Spectroscope]

Figure 2:
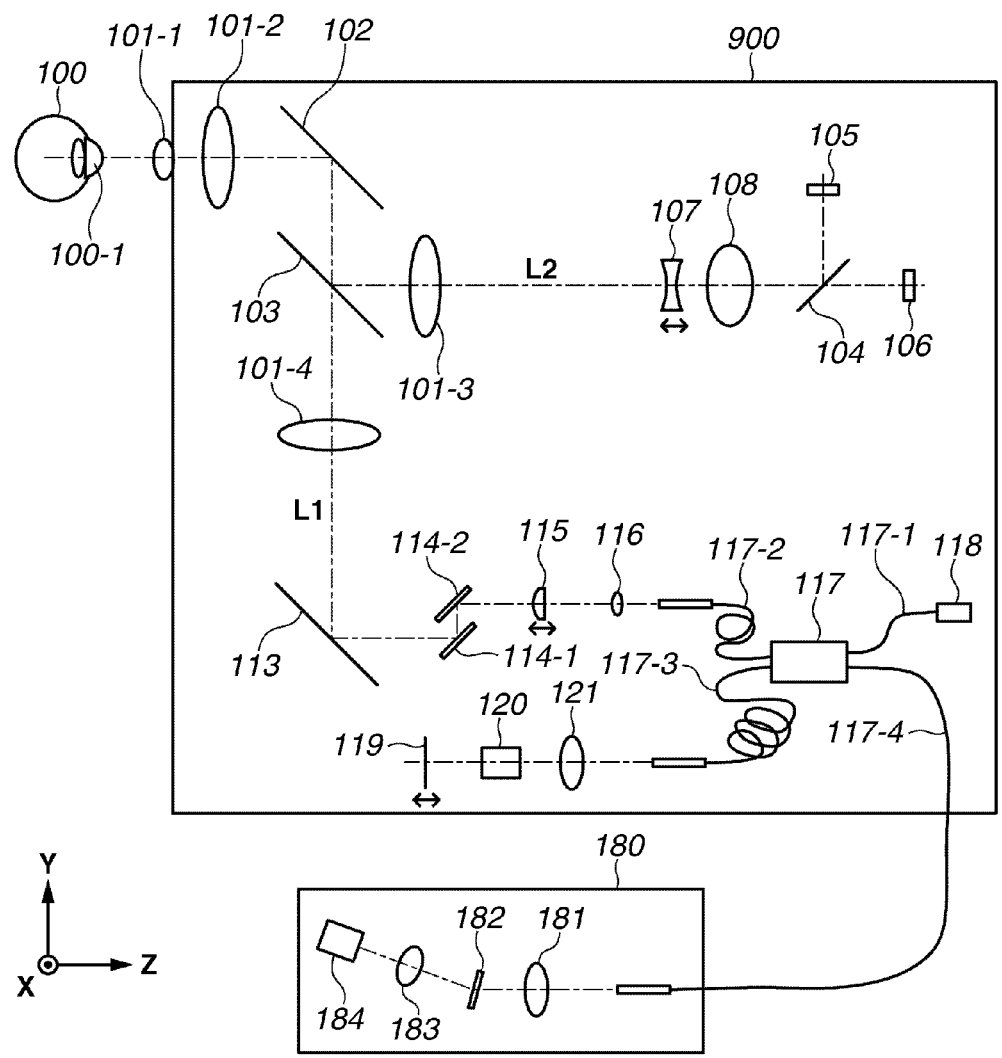
FIG. 2 is a diagram illustrating a configuration of a measurement optical system according to the first exemplary embodiment.

A configuration of the measurement optical system and the spectrometer according to the present exemplary embodiment will be described with reference to FIG. 2.

The interior of the optical head 900 will be described. Objective lenses 101-1 and 101-2 are located opposite a subject's eye 100. A reflecting mirror 102 and a dichroic mirror 103 are arranged on an optical axis of the objective lenses 101-1 and 101-2. By the reflecting mirror 102 and the dichroic mirror 103, light from the object lenses 101-1 and 101-2 is branched into optical paths L1 and L2 of respective different wavelength bands. The optical path L1 is an optical path of an OCT optical system. The optical path L2 is intended for anterior eye observation and for an internal fixation lamp.

The optical path L2 is further branched by a third dichroic mirror 104 into optical paths to a charge-coupled device (CCD) 105 for anterior eye observation and an internal fixation lamp 106 according to respective wavelength bands like described above. Lenses 101-3, 107, and 108 are arranged on the optical path L2. A not-illustrated motor drives the lens 107 for the purpose of a focusing adjustment intended for the internal fixation lamp 106 and anterior eye observation. The CCD 105 has sensitivity to wavelengths of not-illustrated anterior eye observation illumination light. Specifically, the CCD 105 has sensitivity to wavelengths around 780 nm. The internal fixation lamp 106 generates visible light and prompts eye fixation of the subject.

The optical path L1 constitutes the OCT optical system as described above. The optical path L1 is intended to capture a tomographic image of an anterior eye 100-1 of the subject's eye 100. More specifically, the optical path L1 is intended to obtain an interference signal for forming a tomographic image. A lens 101-4, a mirror 113, an X scanner 114-1, a Y scanner 114-2, and lenses 115 (OCT focus lens 115) and 116 are arranged on the optical path L1. The X scanner 114-1 and the Y scanner 114-2 are intended to scan the anterior eye 100-1 of the subject's eye 100 with light. Light from a light source 118 is emitted from a fiber 117-2 connected to a photocoupler 117. A not-illustrated motor drives the lens 115 to focus and adjust the light emitted from the fiber 117-2 on the anterior eye 100-1. By such a focusing adjustment, light from the anterior eye 100-1 is also incident on and forms a spot-like image on the end of the fiber 117-2. The lens 115, also referred to as an OCT focus lens, is an example of a focusing lens.

A configuration of optical paths from the light source 118, a reference optical system, and the spectroscope will be described.

The light source 118, a reference mirror 119, dispersion compensation glass 120, the photocoupler 117 described above, single mode optical fibers 117-1 to 117-4 integrally connected with the photocoupler 117, an lens 121, and the spectroscope 180 constitute a Michelson interferometer.

The light emitted from the light source 118 passes through the optical fiber 117-1 and is split into measurement light on the side of the optical fiber 117-2 and reference light on the side of the optical fiber 117-3 through the photocoupler 117. The measurement light passes through the optical path of the OCT optical system described above. The fundus of the subject's eye 100 to be observed is irradiated with the measurement light. The measurement light is reflected and scattered by the retina, and passes through the same optical path to reach the photocoupler 117.

The reference light passes through the optical fiber 117-3, the lens 121, and the dispersion compensation glass 120 to reach the reference mirror 119. The dispersion compensation glass 120 is inserted to adjust dispersion of the reference light to that of the measurement light. The reference light is reflected by the reference mirror 119 and returns through the same optical path to reach the photocoupler 117. The photocoupler 117 combines the measurement light and the reference light into interference light. Interference occurs when an optical path length of the measurement light and that of the reference light satisfy a predetermined condition. The reference mirror 119 is supported to be adjustable in the optical axis direction by a not-illustrated motor and a not-illustrated drive mechanism. The optical path length of the measurement light varies depending on the anterior eye 100-1. The reference mirror 119 can adjust the optical path length of the reference light to that of the measurement light. The interference light is guided through the optical fiber 117-4 to the spectroscope 180.

The spectroscope 180 includes lenses 181 and 183, a diffraction grating 182, and a line sensor 184. The interference light emitted from the optical fiber 117-4 is converted into generally parallel light through the lens 181. The generally parallel light is spectrally dispersed by the diffraction grating 182, and focused on the line sensor 184 by the lens 183. The line sensor 184 is an example of a light receiving element that receives the interference light and generates and outputs an output signal according to the interference light in the present exemplary embodiment.

Next, the light source 118 will be described. The light source 118 is a super luminescent diode (SLD), which is a typical low coherent light source. The light source 118 has a center wavelength of 855 nm and a wavelength bandwidth of approximately 100 nm. The bandwidth is an important parameter since the bandwidth influences resolution of the resulting tomographic image in the optical axis direction. While an SLD is selected as the light source 118, any type of light source that can emit low coherent light may be used. Examples include an amplified spontaneous emission (ASE) device. In view of eye measurement, near infrared light has a suitable center wavelength. Since the center wavelength influences the resolution of the resulting tomographic image in a lateral direction, the center wavelength can be as short as possible. From both reasons, the center wavelength of 855 nm is employed.

In the present exemplary embodiment, a Michelson interferometer is used as the interferometer. A Mach-Zehnder interferometer may be used instead. Which interferometer to use may be determined according to a difference in light intensity between the measurement light and the reference light. In a case where the difference in light intensity is large, a Mach-Zehnder interferometer can be used. In a case where the difference in light intensity is relatively small, a Michelson interferometer can be used.

[Method for Obtaining Tomographic Image]

A method for obtaining a tomographic image by using the optical tomographic imaging apparatus will be described. The optical tomographic imaging apparatus 200 can obtain a tomographic image of a desired region of the anterior eye 100-1 of the subject's eye 100 by controlling the X scanner 114-1 and the Y scanner 114-2.

Figure 3:
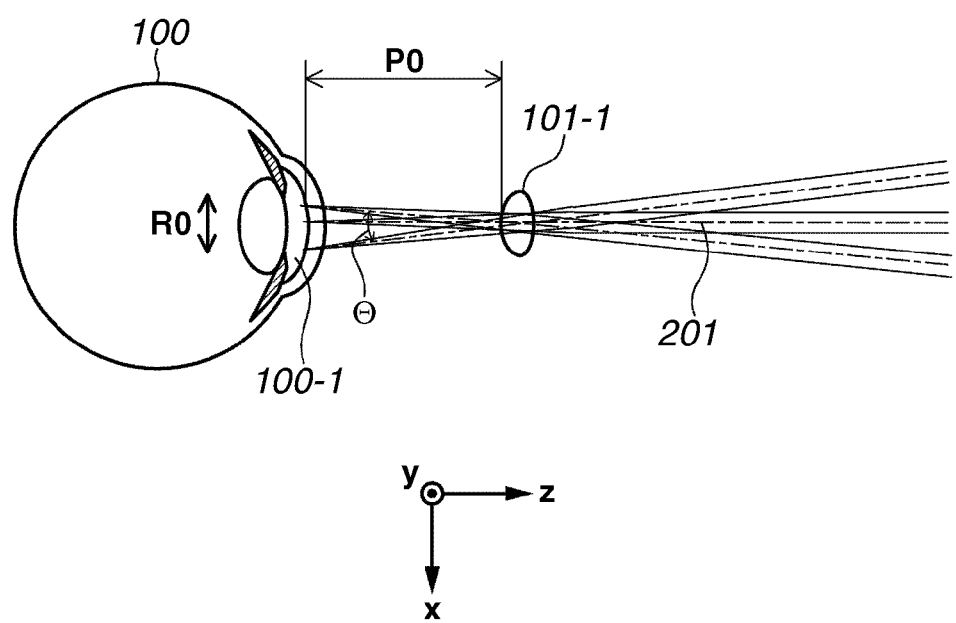
FIG. 3 is an explanatory diagram illustrating a state where an anterior eye of a subject's eye is scanned in an x direction according to the first exemplary embodiment.

FIG. 3 illustrates a state where the subject's eye 100 is irradiated with measurement light 201 and the anterior eye 100-1 is scanned in the x direction. The line sensor 184 captures information about a predetermined number of images from an imaging range of the anterior eye 100-1 in the x direction. A fast Fourier transform (FFT) is performed on a luminance distribution on the line sensor 184 obtained in a position in the x direction. A linear luminance distribution obtained by the FFT is converted into density or color information for monitor display. Such density or color information will be referred to as an A scan image. According to the output signal obtained from the interference light received by the line sensor 184 serving as the light receiving element, the optical tomographic imaging apparatus obtains A scan images. The plurality of A scan images is arranged into a two-dimensional image, which will be referred to as a B scan image. After the plurality of A scan images for constructing a B scan image is obtained, the optical tomographic imaging apparatus moves the scan position in the y direction and performs a scan in the x direction again. In such a manner, the optical tomographic imaging apparatus obtains a plurality of B scan images. The plurality of B scan images or a three-dimensional tomographic image constructed from the plurality of B scan images is displayed on the monitor 928. The operator can use the displayed image(s) to diagnose the subject's eye 100.

The angle of view or the imaging range for obtaining a tomographic image of the anterior eye 100-1 is usually determined according to a scan range R0 in the x direction illustrated in FIG. 4A to be described below. The scan range R0 is determined by a scan angle $\theta$ of the X scanner 114-1 and an imaging distance P0 from the objective lens 101-1 to the anterior eye 100-1 of the subject's eye 100. In other words, to change the size of the imaging range, the scan angle $\theta$ or the imaging distance P0 can be changed. The imaging distance P0 can be easily changed by changing the optical path length of the measurement light, such as by moving the optical head 900 in the z-axis direction. In the present exemplary embodiment, the imaging distance P0 is changed by changing the optical path length of the measurement light of the optical head 900. Such a configuration will be defined as a measurement light optical path length changing unit. There are other configurations for changing the optical path length of the measurement light than that of the present exemplary embodiment. The measurement light optical path length changing unit according to the present exemplary embodiment is defined as a concept covering such configurations.

To obtain a desired interference by combining the measurement light and the reference light, the optical path length of the measurement light and the optical path length of the reference light need to be interlocked to satisfy a predetermined condition as described above. According to the optical path length of the measurement light in the position of the anterior eye 100-1 where the imaging distance is P0, the reference mirror 119 is thus moved to change the optical path length of the reference light.

The reference mirror 119 and a configuration for moving the reference mirror 119 are an example of a reference light optical path length changing unit for changing the optical path length of the reference light according to the present exemplary embodiment. As described above, to obtain interference by the combined light, the optical path length of the reference light needs to be changed according to the optical path length of the measurement light. For example, in the present exemplary embodiment, the personal computer 925 includes a module area that functions as a control unit (also referred to as an "optical path length interlocking unit"). The control unit causes the reference light optical path length changing unit to change the optical path length of the reference light in an interlocking manner with the change of the optical path length of the measurement light by the measurement light optical path length changing unit.

Figure 4A:
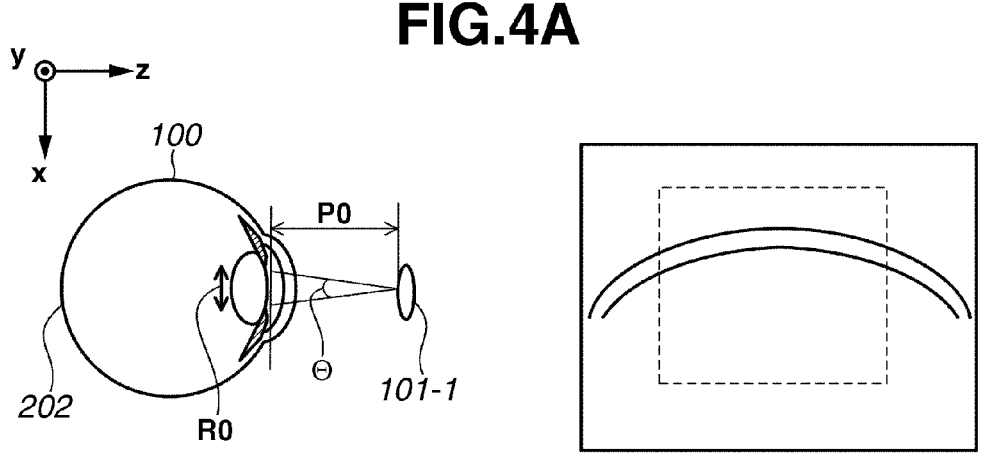
FIGS. 4A, 4B, and 4C are explanatory diagrams illustrating scan ranges in an imaging position of an anterior eye according to the first exemplary embodiment and images obtained according to the scan ranges.
Figure 4B:
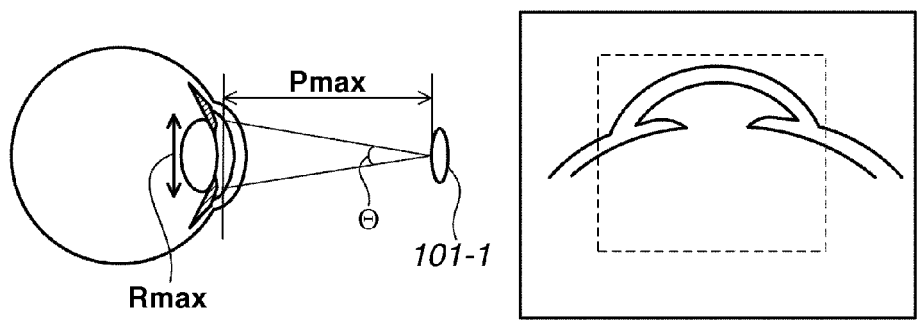
Figure 4C:
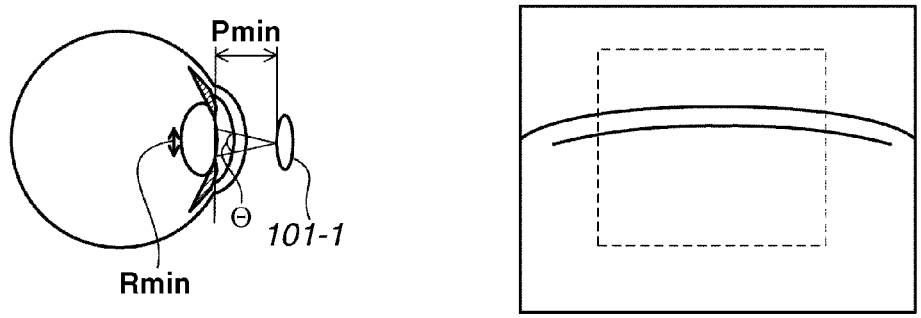

FIGS. 4A, 4B, and 4C illustrate diagrams illustrating the scan ranges in the position of the anterior eye 100-1 when the imaging distance P0 is changed, and corresponding tomographic images displayed in the respective angles of view. By changing the imaging distance P0 and moving the reference mirror 119 according to the change, the optical tomographic imaging apparatus can change the size of the imaging range of the anterior eye 100-1 without changing the scan angle θ. FIG. 4B illustrates a case where the imaging distance P0 is changed to Pmax to increase the distance between the subject's eye 100 and the optical tomographic imaging apparatus, and the reference mirror 119 is moved to a position equivalent to the imaging distance Pmax. In such a case, the anterior eye 100-1 can be imaged with a wide scan range (angle of view) Rmax. FIG. 4C illustrates a case where the imaging distance P0 is changed to Pmin to reduce the distance between the subject's eye 100 and the optical tomographic imaging apparatus, and the reference mirror 119 is moved to a position equivalent to the imaging distance Pmin. In such a case, the anterior eye 100-1 can be imaged with a magnifying scan range Rmin.

[Measurement Operation Screen]

Next, a measurement operation screen according to the present exemplary embodiment will be described with reference to FIGS. 5 and 6. FIG. 5 is a diagram illustrating an example of a measurement operation screen 1000 according to the present exemplary embodiment. FIG. 6 is a diagram illustrating another example of the measurement operation screen 1000 according to the present exemplary embodiment.

An anterior eye observation screen 1101 displays an anterior eye image 1102 obtained by the CCD 105 for anterior eye observation. A tomographic image display screen 1301 is intended to check a tomographic image obtained. L and R buttons 1001 are intended to switch between subject's left and right eyes. The L and R buttons 1001 are pressed to move the optical head 900 to initial positions for the left and right eyes, respectively. When the operator operates the mouse included in the input unit 929, a position of a mouse cursor 1002 moves. This optical tomographic imaging apparatus is configured so that a mouse cursor position detection unit can change an alignment unit according to the position of the mouse cursor 1002. The mouse cursor position detection unit calculates the position of the mouse cursor 1002 from a pixel position of the mouse cursor 1002 on-screen. Ranges are set on the measurement operation screen, and correspondence between the set ranges and alignment drives is set in advance. In a case where the mouse cursor 1002 falls within the pixels of a set range, alignment defined for the set range can be performed. Alignment operations by the mouse are performed by rotating a wheel of the mouse.

Sliders 1103 and 1203 arranged near the respective images are intended for adjustment. The slider 1103 is intended to specify the imaging distance P0 to the subject's eye 100. When the slider 1103 is moved, a character 1003 in the anterior eye observation screen 1101 changes in size in an interlocking manner. The size of the character 1003 is also interlocked with a change in the size of the imaging range (angle of view) of the anterior eye 100-1, whereby the lens 107 for anterior eye observation is moved to a predetermined position. The lens 107 is an example of an anterior eye observation unit including a focus lens that performs focusing on the anterior eye 100-1 according to the present exemplary embodiment. An upper limit of the slider 1103 corresponds to the imaging range Rmax of the anterior eye 100-1 described above. A lower limit of the slider 1103 corresponds to the imaging range Rmin of the anterior eye 100-1. The slider 1203 is intended to perform an OCT focus adjustment. The OCT focus adjustment is an adjustment for moving the lens 115 in the direction indicated by an arrow illustrated in FIG. 2 to make a focusing adjustment with respect to the anterior eye 100-1. The sliders 1103 and 1203 are also configured to move in an interlocking manner with alignment operations performed in the respective images by using the mouse. More specifically, the control unit (also referred to as a "focus interlocking unit") of the personal computer 925 causes the OCT focus lens 115 to perform focusing on the anterior eye 100-1 in an interlocking manner with the change of the optical path length of the measurement light by the measurement light optical path length changing unit, either independent of or in an interlocking manner with the OCT focus adjustment by the slider 1203. The focusing operation of the anterior eye observation unit on the anterior eye 100-1 needs to be performed according to a change in the optical path length of the measurement light, which is accompanied by a change in the imaging distance P0. In the present exemplary embodiment, the foregoing control unit (also referred to as an "anterior eye focusing interlocking unit") causes the anterior eye observation unit to perform focusing on the anterior eye 100-1 in an interlocking manner with the change of the optical path length of the measurement light by the measurement light optical path length changing unit.

FIG. 6 illustrates the measurement operation screen 1000 in which the slider 1103 illustrated in FIG. 5 is replaced with imaging range selection buttons 1004. Settings include a standard (R0=6 mm×6 mm), a maximum (Rmax=9 mm×9 mm), and a minimum (Rmin=3 mm×3 mm). In a case where the operator selects any one of the imaging range selection buttons 1004, the optical tomographic imaging apparatus can change the size of the imaging range of a tomographic image accordingly. The optical tomographic imaging apparatus can change the size of the imaging range even in a case where the operator makes such a selection without an anterior eye image 1102 obtained.

[Flow for Obtaining Tomographic Image of Anterior Eye]

A flow for obtaining a tomographic image of an anterior eye 100-1 by using the OCT apparatus according to the present exemplary embodiment will be described with reference to FIG. 7. FIG. 7 is a flowchart illustrating a measurement flow according to the present exemplary embodiment. The flowchart illustrates operations of the operator and the personal computer 925.

In step S101, the personal computer 925 starts the present measurement flow. In step S102, the optical tomographic imaging apparatus obtains an anterior eye image 1102 according to an instruction from the personal computer 925. The subject's eye 100 is illuminated with not-illustrated anterior eye illumination light. Reflected light passes through the object lenses 101-1 and 101-2 and the optical path L2 described above, and forms an image on the CCD 105. The anterior eye image 1102 formed on the CCD 105 is read by a not-illustrated CCD control unit, amplified, subjected to analog-to-digital (A/D) conversion, and input to a calculation unit. The anterior eye image 1102 input to the calculation unit is taken into the personal computer 925.

In step S103, the operator gives the slider 1103 an instruction to change the size of the imaging range to a desired size by using the input unit 929 which gives instructions to the personal computer 925. A bar of the slider 1103 moves on-screen. According to the operator's instruction, the personal computer 925 serving as an example of the control unit moves the optical head 900 in the optical axis direction to a distance corresponding to the changed size. In step S104, the personal computer 925 serving as an example of the control unit performs control to move the reference mirror 119, according to the movement of the optical head 900, to a position corresponding to the distance to which the optical path length of the measurement light is changed. As a result, a coherence gate is adjusted so that an anterior eye tomographic image is located within an imaging frame. The personal computer 925 may move the lens 107 along with the movement of the reference mirror 119. When the personal computer 925 moves the optical head 900 and the reference mirror 119 in an interlocking manner according to the instruction to change the size of the imaging range, the personal computer 925 may also move the OCT focus lens 115 in an interlocking manner to change the focusing position. Instead of moving the reference mirror 119 in an interlocking manner, the personal computer 925 may move the OCT focus lens 115 in an interlocking manner. In such a case, step S106 to be described below may be omitted. The personal computer 925 may simultaneously move such members. The personal computer 925 may move such members with a time difference.

In step S105, the personal computer 925 serving as an example of the control unit moves the optical head 900 with respect to the anterior eye 100-1 according to instructions from the operator, thereby positioning (aligning) the optical head 900 to the anterior eye 100-1. The positioning may be performed by moving the subject's face support with respect to the optical head 900. Aside from the operator's manual operations, the optical head 900 may move automatically. Specifically, the personal computer 925 detects a pupil position of the subject's eye 100 by image processing from the anterior eye image 1102 captured by the CCD 105. Based on the detected pupil position, the personal computer 925 can find out an alignment position relationship between the optical tomographic imaging apparatus and the subject's eye 100. The personal computer 925 can drive the optical head 900 by using a not-illustrated XYZ stage so that the detected pupil position of the subject's eye 100 comes to an ideal position. The personal computer 925 may keep track of the anterior eye 100-1 while capturing a tomographic image. In such a case, the operator can continue monitoring the anterior eye 100-1 of the subject's eye 100 with improved convenience.

In step S106, the operator gives the slider 1203 an instruction to change the focusing position of the anterior eye tomographic image by using the input unit 929. A bar of the slider 1203 moves on-screen. According to the operator's instruction, the personal computer 925 serving as an example of the control unit performs control to move the OCT focus lens 115. In such a manner, an OCT focus can be adjusted. In step S107, the operator presses a capture button 1005 by using the input unit 929. According to the operator's instruction, the personal computer 925 serving as an example of the control unit performs control to obtain a tomographic image of the anterior eye 100-1. In step S108, the personal computer 925 serving as an example of a display control unit causes the monitor 928 to display the tomographic image of the anterior eye 100-1. In step S108, the personal computer 925 may correct the tomographic image of the anterior eye 100-1 and cause the monitor 928 to display the corrected tomographic image. In step S109, the personal computer 925 ends the present measurement flow.

Note that the tomographic image obtained in step S107 may include a wider or narrower range of regions than, for example, a tomographic image obtained at the standard imaging distance P0 does in the screen of the same size. As will be described below, the correction is an operation for enlarging or reducing a display range (angle of view) so that the regions included in such captured images are displayed in the same size as that of the region obtained at the imaging distance P0. The above operation is performed by a module area of the personal computer 925, the module area functioning as an image correction unit for correcting and changing a display mode of an image. A module area functioning as the display control unit, which is included in the control unit, displays a cursor or a display form for giving an instruction to change the imaging range on the display unit.

Figure 8A:
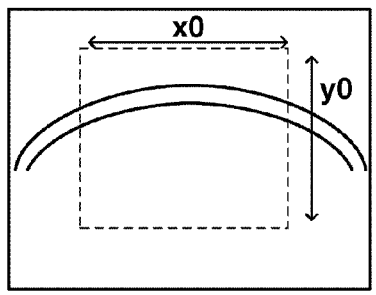
FIGS. 8A, 8B, 8C, 8D, 8E, and 8F are diagrams illustrating display examples of tomographic images of an anterior eye according to the first exemplary embodiment and display examples of the images corrected.
Figure 8B:
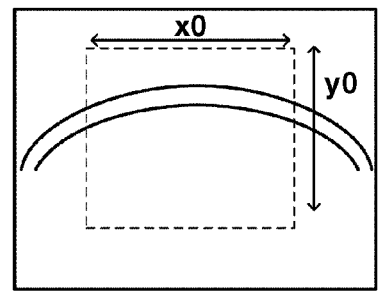
Figure 8C:
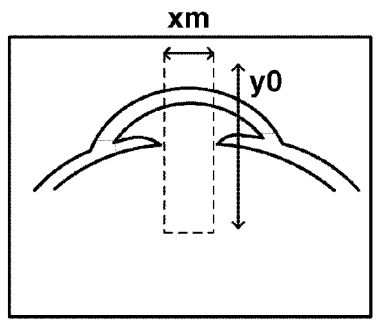
Figure 8D:
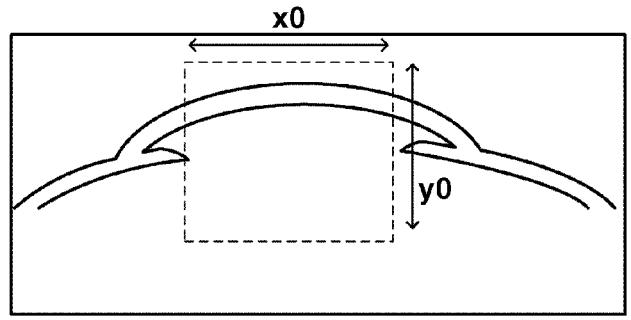
Figure 8E:
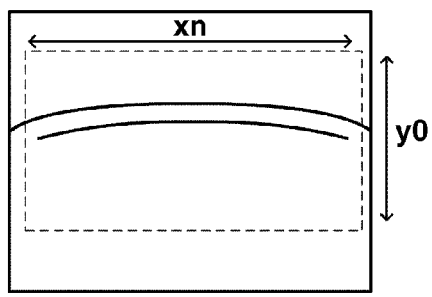
Figure 8F:
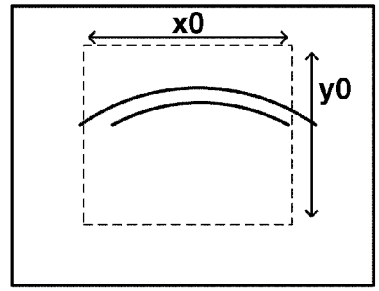

In a case where the imaging distance P0 is greater than the standard imaging distance, the tomographic image of the anterior eye 100-1 becomes narrower only in the lateral direction without a change in tomographic depth. In a case where the imaging distance P0 is smaller than the standard imaging distance, the tomographic image becomes wider only in the lateral direction without a change in the tomographic depth. FIGS. 8A, 8B, 8C, 8D, 8E, and 8F illustrate examples where display images of tomographic images of an anterior eye 100-1 are corrected. FIG. 8A illustrates a tomographic image of the anterior eye 100-1 with a lateral field of view x0 corresponding to the imaging distance P0. In a case where the imaging distance P0 increases to Pmax, the lateral field of view x0 decreases to xm as illustrated in FIG. 8C. As illustrated in FIG. 8D, the lateral field of view xm can be easily converted into the field of view x0 and displayed by using a known image processing method. A tomographic image corresponding to the imaging distance Pmin can be similarly processed and displayed as illustrated in FIG. 8F. Various measurements may be performed based on the tomographic images illustrated in FIGS. 8D and 8F. Various measurements may be performed by using the original images illustrated in FIGS. 8C and 8E, multiplied by the respective ratios of the imaging distances P and the lateral fields of view X.

As described above, the optical tomographic imaging apparatus according to the present exemplary embodiment can provide an apparatus with which the operator can specify various imaging ranges and capture images. In other words, an optical tomographic imaging apparatus having various fields of view and high resolution can be provided while maintaining the performance of the optical systems. Since the operating distance between the subject's eye 100 and the optical tomographic imaging apparatus can be changed, burdens on the subject can be relieved by capturing an image with an increased operating distance according to the subject's condition.

[Designating Size of Imaging Range According to Imaging Region]

A second exemplary embodiment will be described with reference to FIG. 9. FIG. 9 is a diagram illustrating an example of a measurement operation screen according to the present exemplary embodiment. In the first exemplary embodiment, the imaging range is set by slider settings. In the present exemplary embodiment, the size of the imaging range can be designated by selecting an imaging region.

Imaging region selection buttons 1006 can select a cornea and an iridocorneal angle. In a case where the cornea is selected, the optical tomographic imaging apparatus captures an image at the maximum distance Pmax to image a wide range. In a case where the iridocorneal angle is selected, the optical tomographic imaging apparatus employs the minimum distance Pmin to image a narrow range in detail. The imaging region selection buttons 1006 include an angle button. In a case where the angle button is clicked, the optical tomographic imaging apparatus enters an iridocorneal angle imaging mode. The character 1003 in the anterior eye observation screen 1101 becomes small to indicate the imaging range corresponding to the imaging distance Pmin. The subsequent operations are similar to those of the first exemplary embodiment. An imaging operation is performed in a manner similar to that of the first exemplary embodiment.

The light source 118 for OCT measurement has a center wavelength of 855 nm. In a case where the iridocorneal angle is selected to be imaged, the light source 118 may be switched to one having a center wavelength of around 1300 nm. Longer wavelengths lower the lateral resolution of the resulting tomographic image, but increase invasion depth with respect to less transparent tissues included in the iridocorneal angle portion such as the sclera and the iris.

[Designating Size of Imaging Range of Tomographic Image of Fundus]

Figure 10:
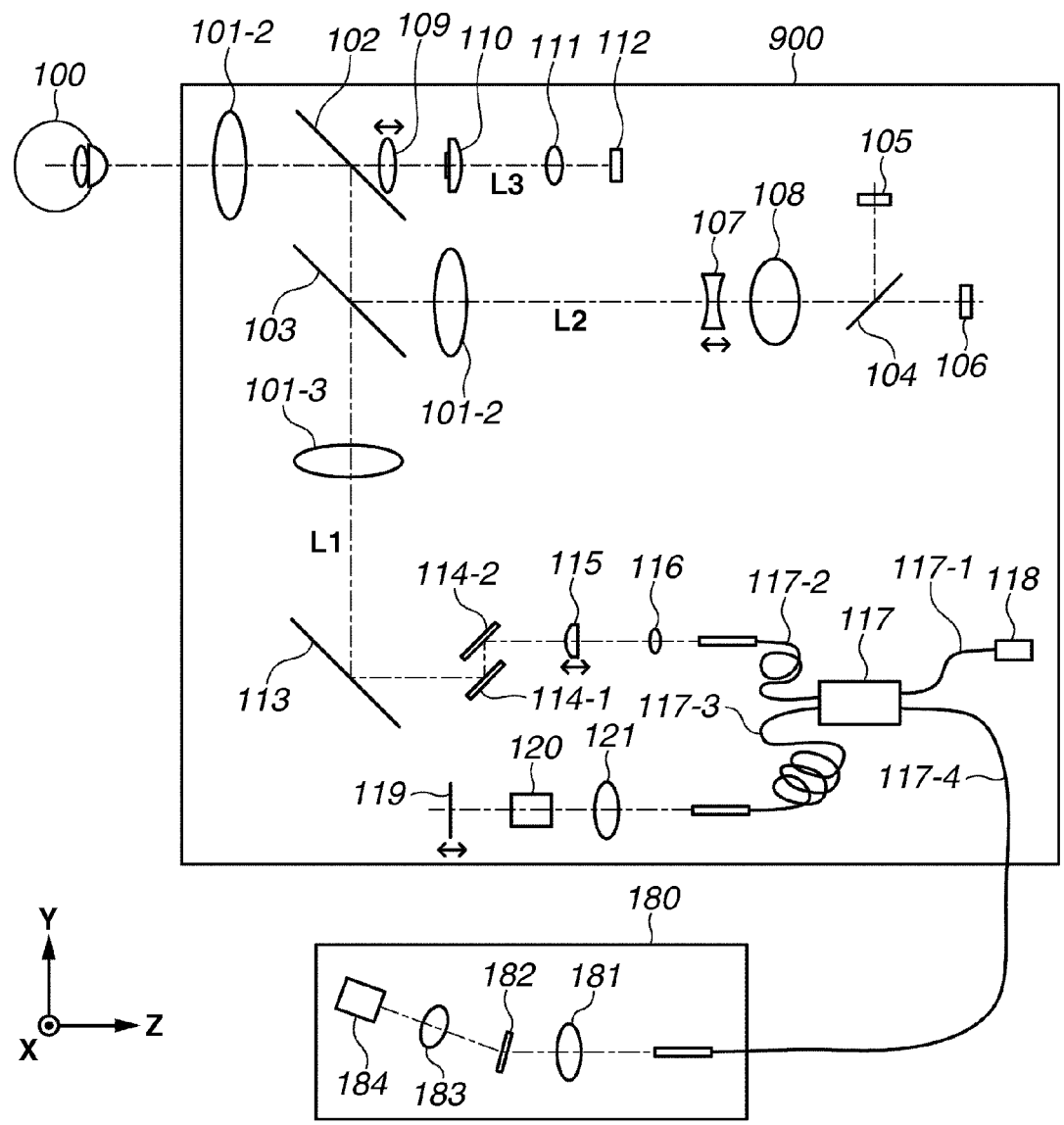
FIG. 10 is a diagram illustrating an entire optical tomographic imaging apparatus according to a third exemplary embodiment.

Fundus imaging using an optical tomographic imaging apparatus (OCT apparatus) according to a third exemplary embodiment will be described with reference to FIG. 10. FIG. 10 is a diagram illustrating the entire optical tomographic imaging apparatus according to the third exemplary embodiment. FIG. 10 differs from FIG. 2 in that the reflecting mirror 102 is replaced with a dichroic mirror, and an optical path L3 of an alignment optical system (anterior eye observation system) is provided. A lens 109, a split prism 110, a lens 111, and a CCD 112 are arranged on the optical path L3. FIG. 10 illustrates a state where the objective lens 101-1 for anterior eye measurement is detached. The other components of the optical tomographic imaging apparatus are similar to those of FIG. 2. The objective lens 101-1 may be configured as an adapter that can be detachably attached to the subject's eye side of the objective lens 101-2. The objective lens 101-1 may be removably inserted into the optical path. In such a case, the objective lens 101-1 may be configured so that the objective lens 101-1 is inserted into the optical path in a case where an anterior eye imaging mode is selected by a not-illustrated imaging mode selection unit. The objective lens 101-1 may be removed from the optical path in a case where a fundus imaging mode is selected.

[Method for Capturing Tomographic Image of Fundus]

A method for capturing a tomographic image by using the optical tomographic imaging apparatus will be described. The optical tomographic imaging apparatus 200 can capture a tomographic image of a desired region on a fundus 100-2 of the subject's eye 100 by controlling the X scanner 114-1 and the Y scanner 114-2.

Figure 11:
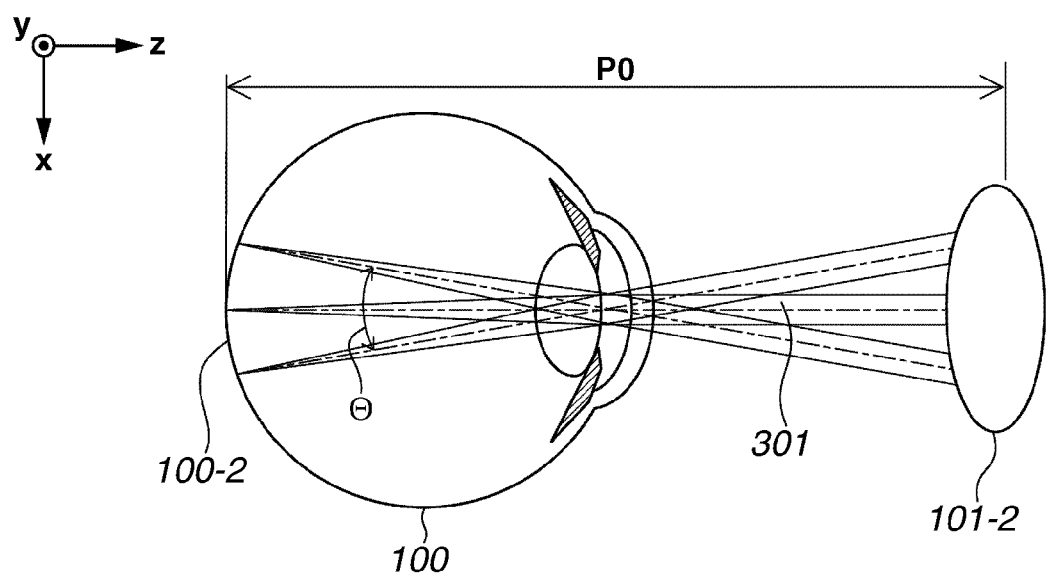
FIG. 11 is a diagram illustrating a state where a fundus is scanned in an x direction according to the third exemplary embodiment.

FIG. 11 illustrates a state where the subject's eye 100 is irradiated with measurement light 301 and the fundus 100-2 is scanned in the x direction. The line sensor 184 captures information about a predetermined number of images from the imaging range of the fundus 100-2 in the x direction. An FFT is performed on a luminance distribution on the line sensor 184 obtained in a position in the x direction. A linear luminance distribution obtained by the FFT is converted into density or color information for monitor display. Such density or color information is referred to as an A scan image. A plurality of A scan images is arranged into a two-dimensional image, which is referred to as a B scan image. After the plurality of A scan images for constructing a B scan image is imaged, the optical tomographic imaging apparatus moves the scan position in the y direction and performs a scan in the x direction again. In such a manner, the optical tomographic imaging apparatus obtains a plurality of B scan images. The plurality of B scan images or a three-dimensional tomographic image constructed from the plurality of B scan images is displayed on the monitor 928. The operator can use the displayed image(s) to diagnose the subject's eye 100. A scan range R0 in the x direction is determined by the scan angle θ of the X scanner 114-1 and the imaging distance P0 from the objective lens 101-2 to the fundus 100-2 of the subject's eye 100. The position of the fundus 100-2 at the imaging distance P0 is a tomographic imaging position to which the reference mirror 119 is moved to generate interference light with reference light.

Figure 12A:
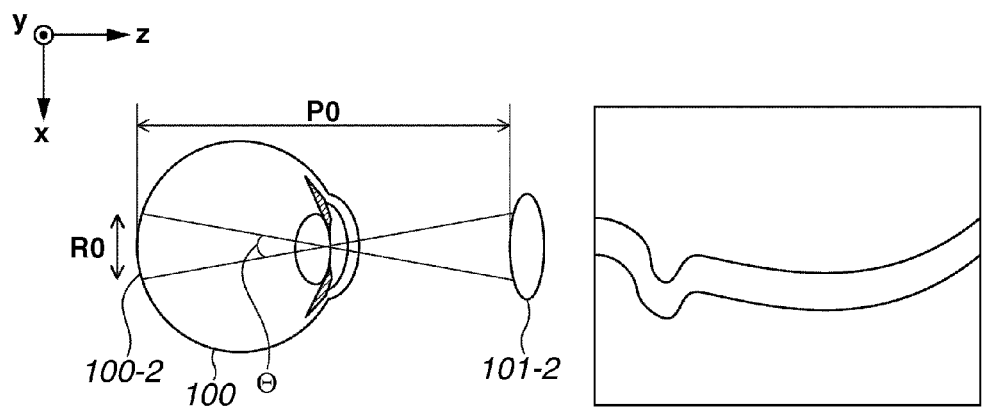
FIGS. 12A, 12B, and 12C are diagrams illustrating scan ranges in an imaging position of a fundus according to the third exemplary embodiment.
Figure 12B:
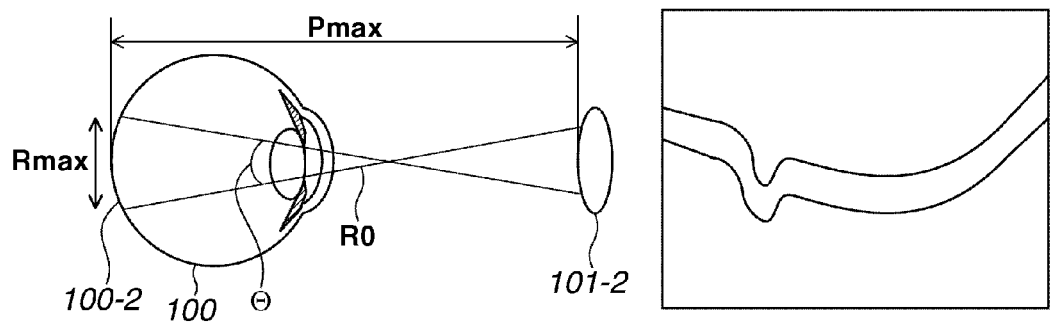
Figure 12C:
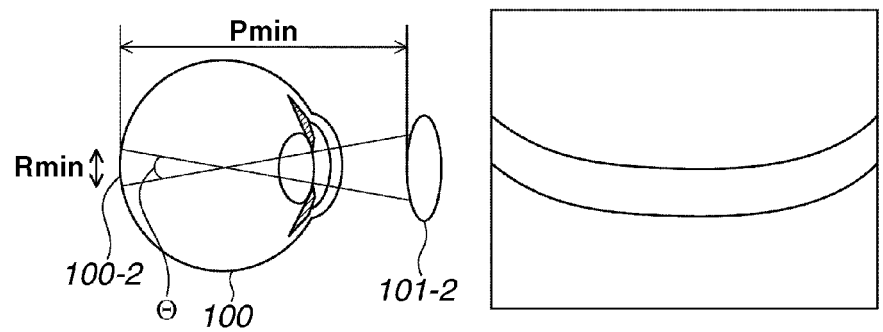

FIGS. 12A, 12B, and 12C are diagrams illustrating the scan ranges in the imaging position of the fundus 100-2 when the imaging distance P0 is changed. The reference mirror 119 can be moved to change the imaging distance P0 and the imaging range of the fundus 100-2 without changing the scan angle θ. FIG. 12B illustrates a case where the reference mirror 119 is moved to a position equivalent to the imaging distance Pmax to increase the distance between the subject's eye 100 and the optical tomographic imaging apparatus. In such a case, the fundus 100-2 can be imaged with a wide scan range Rmax. FIG. 12C illustrates a case where the reference mirror 119 is moved to a position equivalent to the imaging distance Pmin to reduce the distance between the subject's eye 100 and the optical tomographic imaging apparatus. In such a case, the fundus 100-2 can be imaged with a magnified scan range Rmin. FIG. 12A illustrates a case where the imaging distance P0 is in a standard position. In the standard position, a scanning center position of the measurement light generally coincides with the pupil of the subject's eye 100, in which case the measurement light is least likely to be shaded by the pupil.

Figure 13A:
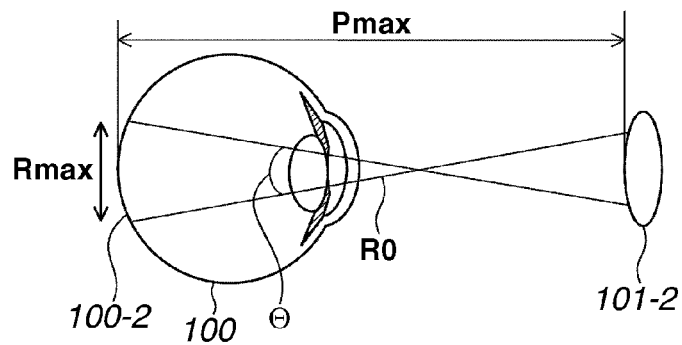
FIGS. 13A, 13B, 13C, and 13D are diagrams illustrating a method for determining a scan range in the imaging position of a fundus in a case where the subject's eye has a small pupil diameter according to the third exemplary embodiment.
Figure 13B:
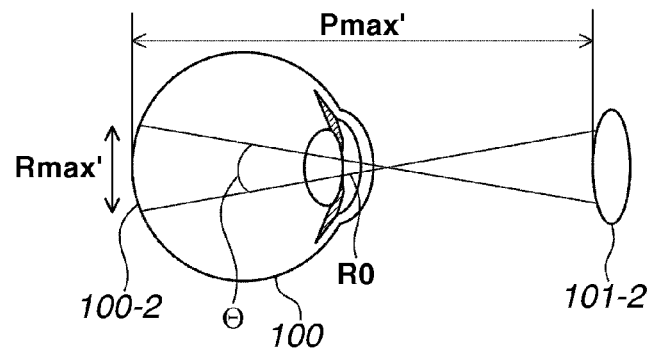

FIGS. 13A, 13B, 13C, and 13D are diagrams illustrating scan ranges when the pupil diameter is smaller than that of the subject's eye 100 of FIGS. 12A, 12B, and 12C. FIG. 13A illustrates a case where the reference mirror 119 is moved to the position equivalent to the imaging distance Pmax like FIG. 12B. Since the pupil diameter is smaller, the measurement light is shaded by the pupil. In such a case, as illustrated in FIG. 13B, the imaging distance Pmax needs to be reduced to an imaging distance Pmax' where the measurement light is not shaded by the pupil. The resulting imaging range is Rmax'.

Figure 13C:
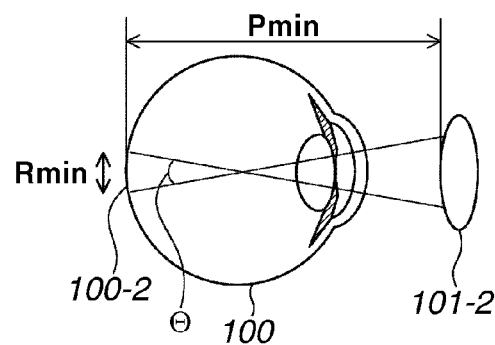
Figure 13D:
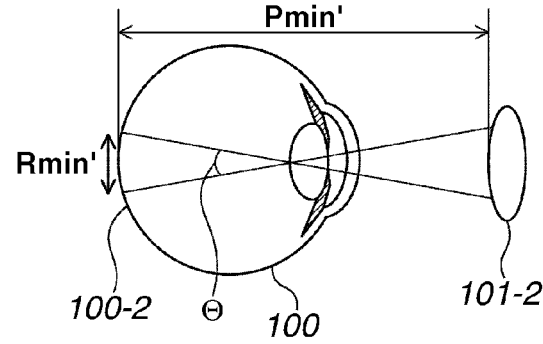

FIG. 13C illustrates a case where the reference mirror 119 is moved to the position equivalent to the imaging distance Pmin like FIG. 12C. Since the pupil diameter is smaller, the measurement light is shaded by the pupil. In such a case, as illustrated in FIG. 13D, the imaging distance Pmin needs to be increased to an imaging distance Pmin' where the measurement light is not shaded by the pupil. The resulting imaging range is Rmin'. In such a manner, when changing the imaging range by changing the optical path length of the measurement light during fundus imaging, the optical tomographic imaging apparatus needs to determine the limits of the imaging range according to the pupil diameter of the subject's eye 100. The optical tomographic imaging apparatus can calculate the limits of the imaging range from the width of the measurement light 301, a difference between the standard imaging distance P0 and the imaging distance, the scan angle θ of the measurement light 301, and the size of the cornea of the subject's eye 100.

[Measurement Operation Screen for Displaying Tomographic Image of Fundus]

Figure 14A:
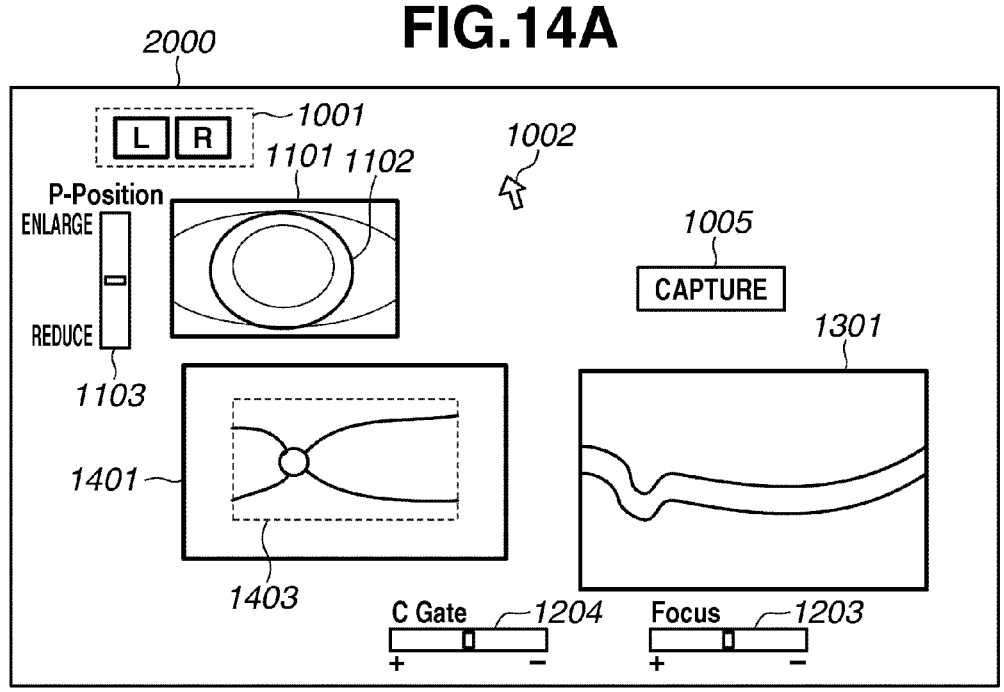
FIGS. 14A and 14B are diagrams illustrating examples of a measurement operation screen according to the third exemplary embodiment.

Next, a measurement operation screen according to the present exemplary embodiment will be described with reference to FIG. 14A. FIG. 14A illustrates a measurement operation screen 2000 during fundus imaging. The measurement screen 2000 has basically the same configuration as that of FIG. 5. The tomographic image display screen 1301 displays a tomographic image of the fundus 100-2 instead of a tomographic image of the anterior eye. In FIG. 5, the anterior eye observation screen 1101 displays an observation image obtained by the CCD 105. In the present exemplary embodiment, the anterior eye observation screen 1101 displays an observation image of the anterior eye obtained by the CCD 112. In the present exemplary embodiment, the CCD 105 obtains an observation image of the fundus 100-2, which is displayed on a fundus observation screen 1401. The fundus observation screen 1401 may display a pseudo scanning laser ophthalmoscopy (SLO) image obtained by controlling the X scanner 114-1 and the Y scanner 114-2 for fundus observation and scanning the fundus 100-2 with the measurement light 301. In such a case, the optical path L2 illustrated in FIG. 10 may be omitted.

Sliders 1103, 1203, and 1204 arranged near the respective images are intended for adjustment. The slider 1103 is intended to specify the imaging distance with respect to the subject's eye 100. When the slider 1103 is moved, a character 1403 in the fundus observation screen 1401 changes in size in an interlocking manner. The size of the character 1403 is also interlocked with the imaging range of the fundus 100-2, whereby the OCT focus lens 115 is moved to a predetermined position. An upper limit of the slider 1103 corresponds to the imaging range Rmax of the fundus 100-2. A lower limit of the slider 1103 corresponds to the imaging range Rmin of the fundus 100-2. In a case where the pupil diameter of the subject's eye 100 calculated from the observation image of the anterior eye obtained by the CCD 112 is small, the upper and lower limits of the moving range of the slider 1103 are limited to Rmax' and Rmin' according the pupil diameter. The slider 1204 is intended for reference mirror adjustment. The reference mirror adjustment refers to an adjustment for moving the reference mirror 119 in the direction indicated by an arrow illustrated in FIG. 10. The sliders 1103, 1203, and 1204 are configured to move in an interlocking manner with alignment operations performed in the respective images by using the mouse.

[Flow for Obtaining Tomographic Image of Fundus]

Figure 15:
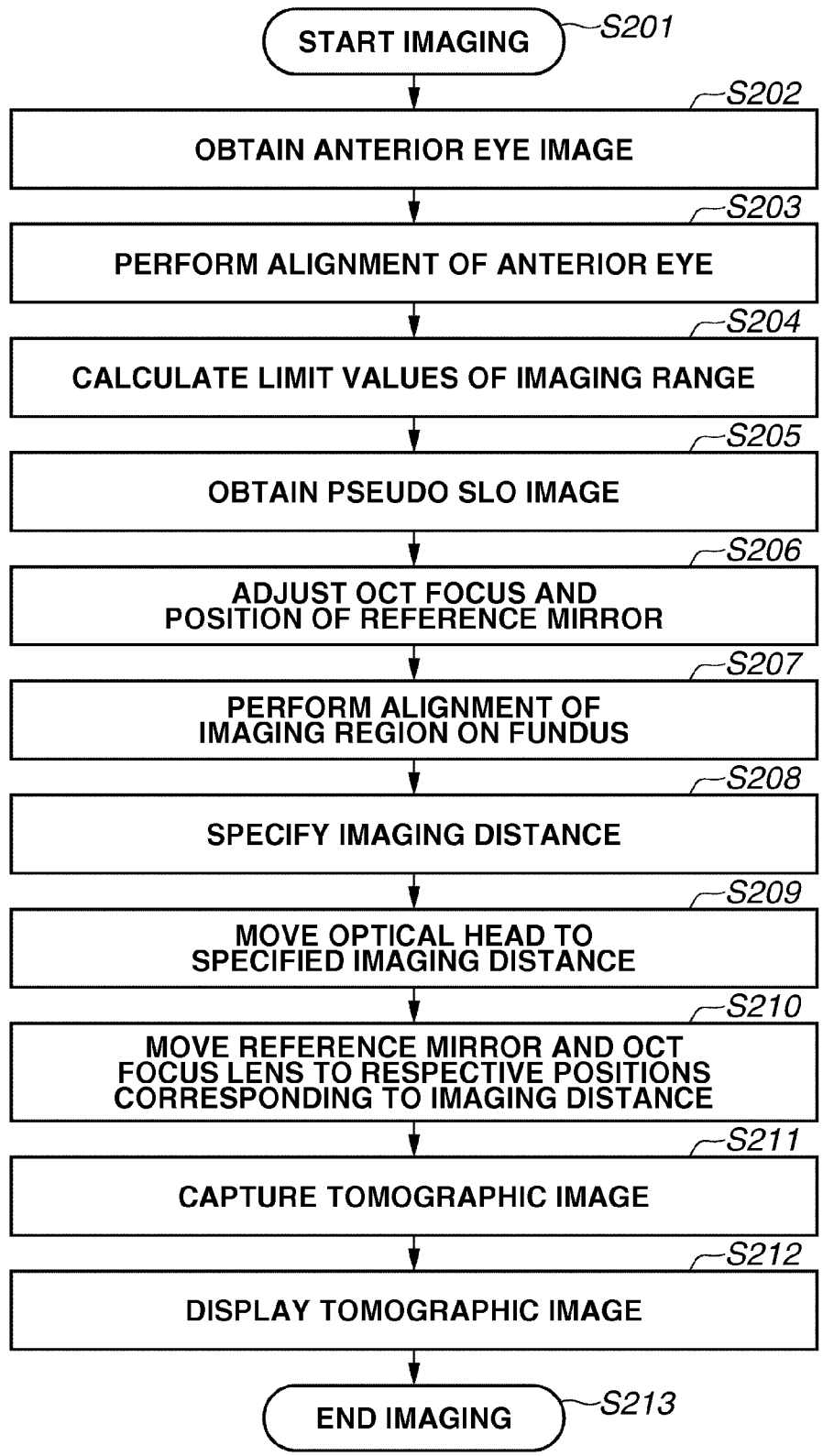
FIG. 15 is a flowchart illustrating a measurement flow according to the third exemplary embodiment.

A method for obtaining a tomographic image by using the OCT apparatus according to the present exemplary embodiment and a method for processing the tomographic image will be described with reference to FIG. 15. FIG. 15 is a flowchart illustrating operations of the operator and the personal computer 925.

In step S201, the personal computer 925 starts imaging. In step S202, the personal computer 925 detects, by image processing, the pupil position of the subject's eye 100 from an anterior eye image 1102 captured by the CCD 112. The personal computer 925 can thus find out an alignment positional relationship between the optical tomographic imaging apparatus and the subject's eye 100. In step S203, the optical tomographic imaging apparatus drives the optical head 900 by using a not-illustrated XYZ stage to perform alignment of the anterior eye so that the detected pupil position of the subject's eye 100 comes to an ideal position. The optical tomographic imaging apparatus can constantly monitor the anterior eye of the subject's eye 100 and correct a misalignment while capturing a tomographic image.

In step S204, the personal computer 925 calculates the pupil diameter of the subject's eye 100 from the anterior eye image 1102, and calculates the limit values of the imaging range Rmax' and Rmin'.

In step S205, the optical tomographic imaging apparatus obtains a pseudo SLO image. In step S206, the operator adjusts the slider 1203 for OCT focusing while observing the pseudo SLO image on the measurement operation screen 2000. The operator also adjusts the slider 1204 to adjust the position of the reference mirror 119 while observing a tomographic image obtained with the pseudo SLO image. In step S207, the operator moves the external fixation lamp 324 or the internal fixation lamp 106 to guide fixation of the subject's eye 100 and performs alignment of the imaging region on the fundus 100-2 while observing the pseudo SLO image. By the foregoing steps S201 to S207, the optical tomographic imaging apparatus becomes ready to obtain a tomographic image of the fundus 100-2 of the subject's eye 100 at the standard imaging distance P0.

In step S208, the operator specifies an imaging distance by using the input unit 929 which gives instructions to the personal computer 925. In step S209, the personal computer 925 drives the not-illustrated XYZ stage to move the optical head 900 to the specified imaging distance. In step S210, the personal computer 925 moves the reference mirror 119 and the OCT focus lens 115 to respective positions corresponding to the imaging distance. In step S211, the operator presses the capture button 1005 to capture a tomographic image of the fundus 100-2. In step S212, the personal computer 925 displays the tomographic image.

As described above, once the optical tomographic imaging apparatus according to the present exemplary embodiment positions the OCT focus lens 115 and the reference mirror 119 for the imaging distance P0, the operator can change the imaging range by only specifying an imaging distance.

[Designating Size of Imaging Range of Fundus According to Selection of Imaging Region on Fundus]

Figure 14B:
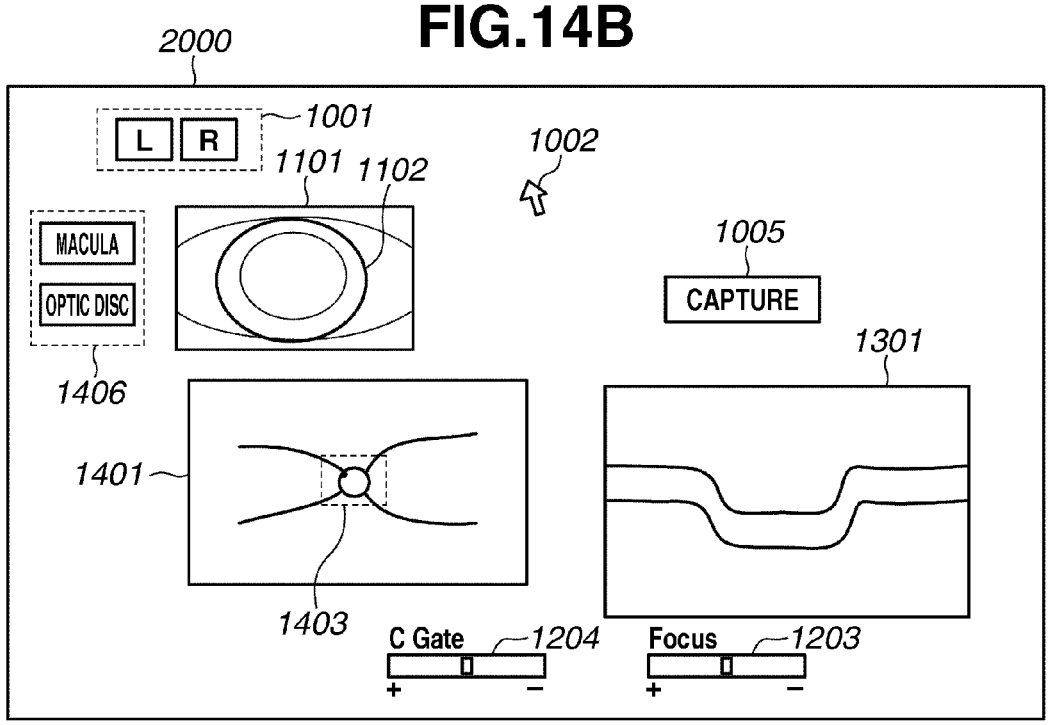

In the present exemplary embodiment, as illustrated in FIG. 14A, the size of the imaging range is designated by using the slider 1103. Like the second exemplary embodiment, the size of the imaging range may be designated by selecting an imaging region. FIG. 14B illustrates an example thereof. Imaging region selection buttons 1406 can select a macula and an optic disc. In a case where the macula is selected, the optical tomographic imaging apparatus may make the imaging distance greater than the standard imaging distance P0 (farther from the fundus 100-2) to image a wide range. The optical tomographic imaging apparatus may capture an image at the standard imaging distance P0. In a case where the optic disc is selected, the optical tomographic imaging apparatus makes the imaging distance smaller than the standard imaging distance P0 (closer to the fundus 100-2) to magnify and image a narrow range in detail. A difference from the imaging operation of FIG. 14A is that the imaging range, which is set by using the slider 1103 in step S207, is selected by using the imaging region selection buttons 1406 instead. The rest of the operation is similar to that of FIG. 14A.

The exemplary embodiments of the present invention are not limited to the foregoing exemplary embodiments, and various changes and modifications may be made without departing from the gist of the foregoing exemplary embodiments. For example, while the foregoing exemplary embodiments have dealt with the case where the object to be measured is the eye, the exemplary embodiments may be applied to objects to be measured other than the eye. Examples include the skin and organs. In such cases, the exemplary embodiments of the present invention are configured as medical apparatuses other than an ophthalmologic apparatus, such as an endoscope. The subject's eye described above can thus be regarded as an object.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-017659 filed Jan. 31, 2013, which is hereby incorporated by reference herein in its entirety.

What is claimed is:

1. An optical tomographic imaging apparatus configured to obtain a tomographic image of an object based on light into which return light from the object irradiated with measurement light and reference light corresponding to the measurement light are combined, the optical tomographic imaging apparatus comprising:
a scanning unit configured to scan the measurement light in the object;
a measurement light optical path length changing unit configured to change an optical path length of the measurement light;
a selection unit configured to select an imaging region of the object;
an instruction unit configured to input an instruction on a size of an imaging range of the tomographic image according to the selected imaging region; and
a control unit configured to control the measurement light optical path length changing unit and the scanning unit according to the instruction.

2. The optical tomographic imaging apparatus according to claim 1,
wherein the measurement light optical path length changing unit includes an optical unit moving mechanism configured to move an optical unit including an optical path of the measurement light with respect to the object, and
wherein the control unit is configured to control the optical unit moving mechanism and the scanning unit according to the instruction.

3. The optical tomographic imaging apparatus according to claim 1,
further comprising a reference light optical path changing unit configured to change an optical path length of the reference light,
wherein the control unit is configured to control the measurement light optical path length changing unit and the reference light optical path length changing unit in an interlocking manner according to the instruction.

4. The optical tomographic imaging apparatus according to claim 1,
further comprising a moving unit configured to move a focusing lens along an optical path, the focusing lens focusing the measurement light on the object,
wherein the control unit is configured to control the measurement light optical path length changing unit and the moving unit in an interlocking manner according to the instruction.

5. The optical tomographic imaging apparatus according to claim 1,
further comprising a display control unit configured to cause a display unit to display a display form for inputting an instruction on selection of the imaging region,
wherein the selection unit is configured to input an instruction on the selection according to an operation by an operation unit.

6. The optical tomographic imaging apparatus according to claim 5,
wherein the object is a fundus of a subject's eye, and
wherein the display control unit is configured to, in a case where a region of the fundus is selected as the imaging region by the selection unit, cause the display unit to display a display form indicating a limit of the size of the imaging range of a tomographic image of the fundus according to a size of a pupil of the subject's eye.

7. The optical tomographic imaging apparatus according to claim 1,
wherein the object is a subject's eye, and
wherein the imaging region includes at least one of a region of an anterior eye of the subject's eye and a region of a fundus of the subject's eye.

8. The optical tomographic imaging apparatus according to claim 1,
wherein the object is an anterior eye of a subject's eye, and
wherein the control unit is configured to control the measurement light optical path length changing unit to increase the optical path length of the measurement light in a case where a cornea of the anterior eye is selected as the imaging region, and to decrease the optical path length of the measurement light in a case where an iridocorneal angle of the anterior of the eye is selected as the imaging region.

9. The optical tomographic imaging apparatus according to claim 1,
wherein the object is a fundus a subject's eye, and
wherein the control unit is configured to control the measurement light optical path length changing unit to increase the optical path length of the measurement light in a case where a macula of the fundus is selected as the imaging region, and to decrease the optical path length of the measurement light in a case where an optic disc of the fundus is selected as the imaging region.

10. A method for controlling an optical tomographic imaging apparatus configured to obtain a tomographic image of an object based on light into which return light from the object irradiated with measurement light and reference light corresponding to the measurement light are combined, the method comprising:
selecting an imaging region of the object;
inputting an instruction on a size of an imaging range of the tomographic image according to the selected imaging region; and
controlling a measurement light optical path length changing unit and a scanning unit according to the instruction, the measurement light optical path length changing unit being configured to change an optical path length of the measurement light and the scanning unit scanning the measurement light in the object.

11. The method according to claim 10,
wherein the measurement light optical path length changing unit includes an optical unit moving mechanism configured to move an optical unit including an optical path of the measurement light with respect to the object, and
wherein the optical unit moving mechanism and the scanning unit are controlled according to the instruction.

12. The method according to claim 10, further comprising controlling the measurement light optical path length changing unit and a reference light optical path length changing unit in an interlocking manner according to the instruction, the reference light optical path length changing unit being configured to change an optical path length of the reference light.

13. The method according to claim 10, further comprising controlling the measurement light optical path length changing unit and a moving unit in an interlocking manner according to the instruction, the moving unit being configured to move a focusing lens along an optical path, the focusing lens focusing the measurement light on the object.

14. The method according to claim 10, further comprising:
causing a display unit to display a display form for inputting an instruction on selection of the imaging region; and
inputting an instruction on the selection according to an operation by an operation unit.

15. The method according to claim 14,
wherein the object is a fundus of a subject's eye, and
wherein, in a case where a region of the fundus is selected as the imaging region, the display unit is caused to display a display form indicating a limit of the size of the imaging range of a tomographic image of the fundus according to a size of a pupil of the subject's eye.

16. The method according to claim 10,
wherein the object is a subject's eye, and
wherein the imaging region includes at least either one of a region of an anterior eye of the subject's eye and a region of a fundus of the subject's eye.

17. The method according to claim 10,
wherein the object is a subject's eye, and
wherein the method further comprises controlling the measurement light optical path length changing unit to increase the optical path length of the measurement light in a case where a cornea of the anterior of the eye is selected as the imaging region, and to decrease the optical path length of the measurement light in a case where an iridocorneal angle of the anterior of the eye is selected as the imaging region.

18. A non-transitory computer-readable storage medium storing a program that causes a computer to perform the method according to claim 10.

* * * * *